United States Patent [19]

Forestier et al.

[11] Patent Number: 5,223,533

[45] Date of Patent: Jun. 29, 1993

[54] NEW BENZYLCYCLANONE DERIVATIVES PROCESS FOR PREPARING THEM AND COSMETIC AND PHARMACEUTICAL COMPOSITIONS CONTAINING THEM

[75] Inventors: Serge Forestier, Claye-Souilly; Alain LaGrange, Chatou; Gerard Lang, Saint-Gratien; Andre Deflandre, Orry-La-Ville; Bernadette Luppi, Sevran, all of France

[73] Assignee: L'Oreal, Paris, France

[21] Appl. No.: 501,260

[22] Filed: Mar. 29, 1990

[30] Foreign Application Priority Data

Mar. 31, 1989 [FR] France ............... 89 04299

[51] Int. Cl.$^5$ .............. A61K 31/34; C07D 307/94
[52] U.S. Cl. ............................. 514/462; 514/473; 549/331; 549/475; 549/477
[58] Field of Search ............ 549/475, 477, 331; 514/473, 462

[56] References Cited

U.S. PATENT DOCUMENTS 3,717,659 2/1973 Sarett et al. ............... 548/543

FOREIGN PATENT DOCUMENTS 2249865 5/1975 France .
61-12660 1/1986 Japan .
2025957 1/1980 United Kingdom .

OTHER PUBLICATIONS

Yin, CA 61:4297b, 1964.
Katsumi et al., "Chem. Pharm. Bull.", 34(4), 1986, pp. 1619–1627.
Rainsford et al., "Anti-Inflammatory and Anti-Rheumatic Drugs", Vol. III, Chapter 4, CRC Press, Inc. 1985, pp. 105–121.
Chemical Abstracts, vol. 56, Abstract No. 8673g (1961).

Primary Examiner—C. Warren Ivy
Assistant Examiner—Ba K. Trinh
Attorney, Agent, or Firm—Jacobson, Price, Holman & Stern

[57] ABSTRACT

The invention relates to the benzylcyclanone derivatives of formula:

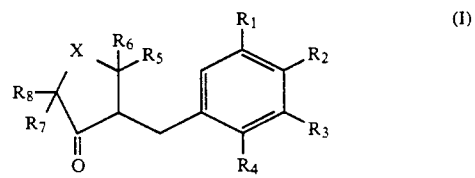

where $R_1$ and $R_3$ denote H, OH, linear or branched $C_1$–$C_8$ alkyl or linear or branched $C_1$–$C_8$ alkoxy, $R_2$ and $R_4$ represent H or OH, at least one of the two being OH, $R_5$, $R_6$, $R_7$ and $R_8$ represent H, $C_1$–$C_{18}$ alkyl, aralkyl or aryl, it being possible for $R_5$ and $R_6$ and/or $R_7$ and $R_8$ to form an optionally substituted, saturated $C_5$–$C_{12}$ ring, X represents O or —$(CR_9R_{10})_n$ with n=1 or 2 and $R_9$ and $R_{10}$ represent H or $CH_3$; if X represents —$(CR_9R_{10})_n$, $R_6$ and $R_8$, with the atoms of the ring to which they are attached, form a bicyclic system having 7 or 8 carbon atoms; if X represents —$(CR_9R_{10})_n$ with n=1, $R_9$ and $R_{10}$=$CH_3$, $R_5$=H and $R_6$ and $R_8$, with the atoms of the ring to which are attached, form a bicyclic system having 7 carbon atoms, $R_7$ can represent a —$CH_2SO_3H$ residue, optionally in salt form.

Process for preparing these compounds and their use as antioxidants and medicinal products for the treatment of skin allergies and inflammations.

16 Claims, No Drawings

NEW BENZYLCYCLANONE DERIVATIVES PROCESS FOR PREPARING THEM AND COSMETIC AND PHARMACEUTICAL COMPOSITIONS CONTAINING THEM

The present invention relates to new benzylcyclanone derivatives, to a process for preparing them and to their use in cosmetic compositions for daily application or for protection against the sun, and in pharmaceutical compositions for the treatment of skin allergies and inflammations.

In the course of his investigations, the Applicant has just discovered that the benzylcyclanone derivatives having the following formula:

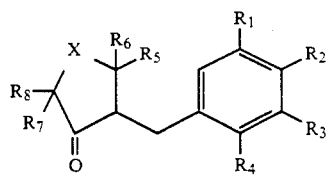

in which:

$R_1$ and $R_3$, which may be identical or different, represent a hydrogen atom, a hydroxyl radical, a linear or branched $C_1$-$C_8$ alkyl residue or a linear or branched $C_1$-$C_8$ alkoxy residue, $R_2$ and $R_4$, which may be identical or different, represent a hydrogen atom or a hydroxyl radical, on the understanding that at least one of the radicals $R_2$ and $R_4$ represents a hydroxyl radical, $R_5$, $R_6$, $R_7$ and $R_8$, which may be identical or different, represent a hydrogen atom, a linear or branched $C_1$-$C_{18}$ alkyl residue, an aralkyl residue such as benzyl, unsubstituted or substituted with a $C_1$-$C_4$ alkyl or $C_1$-$C_4$ alkoxy residue, or an aryl residue such as phenyl, unsubstituted or substituted with a $C_1$-$C_4$ alkyl residue; the substituents $R_5$ and $R_6$ and/or the substituents $R_7$ and $R_8$, with the carbon atom of the ring to which they are attached, can form a saturated ring containing from 5 to 12 carbon atoms, unsubstituted or substituted with one or more linear or branched $C_1$-$C_8$ alkyl residues, X represents either an oxygen atom, or a radical —$(CR_9R_{10})_n$ in which n is equal to 1 or 2 and $R_9$ and $R_{10}$ represent a hydrogen atom or a methyl residue; in the case where X represents a radical —$(CR_9R_{10})_n$, the substituents $R_6$ and $R_8$, with the atoms of the ring to which they are attached, form a bicyclic system containing 7 or 8 carbon atoms; furthermore, when X represents a radical —$(CR_9R_{10})_n$—in which n is equal to 1, $R_9$ and $R_{10}$ represent a methyl residue, $R_5$ representing a hydrogen atom and $R_6$ and $R_8$, with the atoms of the ring to which they are attached, forming a bicyclic system containing 7 carbon atoms, $R_7$ can also represent a —$CH_2$—$SO_3H$ residue, optionally in the form of an alkali metal, alkaline earth metal or amine salt, unexpectedly display excellent antioxidant properties with respect to the peroxidation of polyunsaturated lipids and also with respect to substances capable of undergoing thermally induced or photoinduced oxidation reactions (such as proteins, sugars, pigments, vitamins, polymers, etc.).

In point of fact, the peroxidation of lipids is known to involve the formation of intermediate free radicals, which damage the cell membranes composed, inter alia, of phospholipids and are responsible, in particular, for phenomena of ageing of the skin (A. L. TAPPEL in "Federation Proceedings" Vol. 32, No 8, August 1973).

By virtue of their antioxidant properties the compounds of the invention can hence enable premature ageing of the skin due to the peroxidation of skin lipids to be combated more satisfactorily.

They can also make it possible to provide for better preservation of cosmetic or pharmaceutical compositions containing a fatty phase by avoiding the rancidification of the unsaturated lipids which are present therein and which can be of animal origin, such as lanolin, cetin (spermaceti), beeswax, perhydrosqualene or turtle oil, or of vegetable origin, such as olive oil, castor oil, maize oil, sweet almond oil, avocado oil, shea oil, sunflower oil, soya oil, groundnut oil or coconut or palm-kernel oils, essential fatty acids such as vitamin F and certain essential oils present in perfumes, such as lemon or lavender oil.

They can also enable the oxidative degradation of active compounds present in pharmaceutical compositions (vitamin A, carotenoids, etc.) to be avoided.

The Applicant also discovered, to his extreme surprise, that the compounds of formula (I) above could be used for the treatment of skin allergies and inflammations.

Apart from their good antioxidant properties, the compounds according to the invention possess very good thermal stability.

These compounds also have the advantage of not being toxic or irritant and of being completely harmless with respect to the skin.

The subject of the present invention is the new compounds of the following formula (I'):

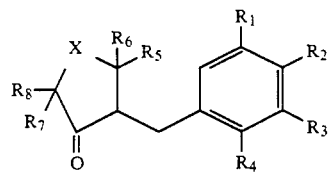

in which:

$R_1$ and $R_3$, which may be identical or different, represent a hydrogen atom, a hydroxyl radical, a linear or branched $C_1$-$C_8$ alkyl residue or a linear or branched $C_1$-$C_8$ alkoxy residue, $R_2$ and $R_4$, which may be identical or different, represent a hydrogen atom or a hydroxyl radical, on the understanding that at least one of the radicals $R_2$ and $R_4$ represents a hydroxyl radical, $R_5$, $R_6$, $R_7$ and $R_8$, which may be identical or different, represent a hydrogen atom, a linear or branched $C_1$-$C_{18}$ alkyl residue, an aralkyl residue such as benzyl, unsubstituted or substituted with a $C_1$-$C_4$ alkyl or $C_1$-$C_4$ alkoxy residue, or an aryl residue such as phenyl, unsubstituted or substituted with a $C_1$-$C_4$ alkyl residue; the substituents $R_5$ and $R_6$ and/or the substituents $R_7$ and $R_8$, with the carbon atom of the ring to which they are attached, can form a saturated ring containing from 5 to 12 carbon atoms, unsubstituted or substituted with one or more linear or branched $C_1$-$C_8$ alkyl residues, X represents either an oxygen atom, or a radical —$(CR_9R_{10})_n$ in which n is equal to 1 or 2 and $R_9$ and $R_{10}$ represent a hydrogen atom or a methyl residue; in the case where X represents a radical —$(CR_9R_{10})_n$, the substituents $R_6$ and $R_8$, with the atoms of the ring to which they are attached, form a bicyclic system containing 7 or 8 carbon atoms; furthermore, when X represents a radical —(CR$_9$R$_{10}$)$_n$— in which n is equal to 1, R$_9$ and R$_{10}$ represent a methyl residue, R$_5$ representing a hydrogen atom and R$_6$ and R$_8$, with the atoms of the ring to which they are attached, forming a bicyclic system containing 7 carbon atoms, R$_7$ can also represent a —CH$_2$—SO$_3$H residue, optionally in the form of an alkali metal, alkaline earth metal or amine salt, with the proviso that, when R$_5$, R$_6$, R$_7$ and R$_8$ denote a methyl radical, X an oxygen atom, R$_2$ a hydrogen atom and R$_4$ a hydroxyl radical, at least one of the radicals R$_1$ and R$_3$ denotes a hydroxyl, alkyl or alkoxy radical.

Among preferred compounds of general formula (I'), the following may be mentioned:

3',4',5'-trihydroxy-4-benzyltetrahydro-2,2,5,5-tetramethyl-3-furanone,
3',5'-di-tert-butyl-4'-hydroxy-4-benzyltetrahydro-2,2,5,5-tetramethyl-3-furanone,
3',5'-diisopropyl-4'-hydroxy-4-benzyltetrahydro-2,2,5,5-tetramethyl-3-furanone,
3',5'-di-tert-butyl-4'-hydroxy-3-benzylcamphor,
3',5'-dimethoxy-4'-hydroxy-3-benzylcamphor,
3',5'-dimethyl-4'-hydroxy-3-benzylcamphor,
3',5'-di-tert-butyl-4'-hydroxy-3-benzylnorcamphor,
3',4',5'-trihydroxy-3-benzylcamphor,
3',5'-diisopropyl-4'-hydroxy-3-benzylcamphor,
3'-methyl-4'-hydroxy-5'-tert-butyl-3-benzylcamphor.

The compounds of formula (I') may be obtained according to several processes.

I. First process

This process consists in reducing a benzylidenecyclanone of formula (II) according to the following reaction scheme:

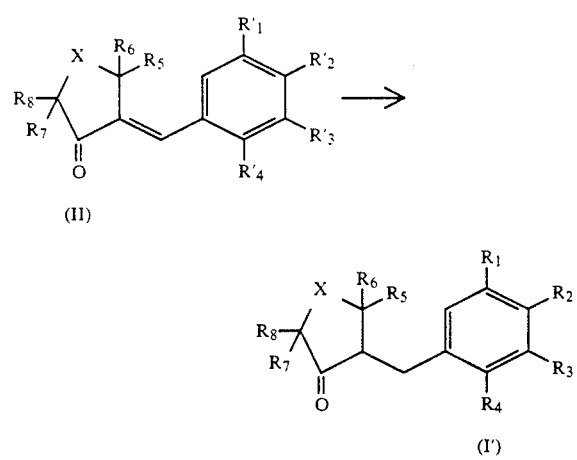

In the compound of formula (II), the substituents R$_5$, R$_6$, R$_7$, R$_8$ and X have the meanings as stated above for the compound of formula (I'), it being possible for R'$_1$, R'$_2$, R'$_3$ and R'$_4$ to represent R$_1$, R$_2$, R$_3$ or R$_4$, respectively, or alternatively an arylalkoxy residue.

The reduction may be carried out either by catalytic hydrogenation, or by hydrogenation in the presence of a hydrogen transfer agent under the conditions described by G. Brieger and R. J. Nestrick in Chemical Reviews Vol. 74 (No. 5) pages 567 to 580, for example, by means of cyclohexene or formic acid in the presence of a catalyst such as palladium on charcoal, optionally in the presence of an inert solvent. The reaction is performed at a temperature between −78° C. and the boiling point of the reaction mixture.

When, in the formula (I'), the cyclanone represents a camphor residue, a mixture of isomers (endo and exo) is obtained. The formation of the more stable isomer can be directed by treating the mixture in alcohol, in a basic medium, preferably with potassium hydroxide or sodium methylate, and heating where appropriate.

The compounds of formula (II) are obtained by condensation of an aromatic aldehyde of formula (III):

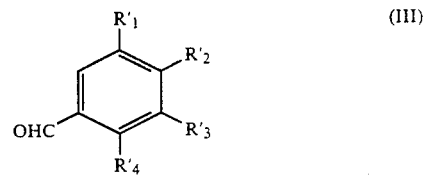

with a cyclanone of formula:

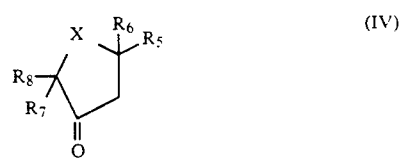

The aldehydes of formula (III) and the cyclanones of formula (IV) in which the substituents R'$_1$ to R'$_4$, R$_5$ to R$_8$ and X have the meanings stated above for the compound of formula (II) are known compounds.

The condensation of the aldehyde (III) with the cyclanone (IV) may be performed according to one of the following two methods:

a) First method

The condensation is performed in the presence of an alkali metal alcoholate such as sodium methylate or potassium tert-butylate, in a solvent such as toluene, 1,2-dimethoxyethane or 1,2-diethoxyethane, at a temperature between −78° C. and the boiling point of the solvent. The condensation may also be performed in the presence of an inorganic base such as an alkali metal hydroxide, amide or hydride, in a solvent such as 1,2-dimethoxyethane or toluene, at a temperature between 0° C. and the boiling point of the reaction mixture.

b) Second method

The condensation of the aldehyde (III) with the cyclanone (IV) is performed in the presence of a borane of the following formula (V):

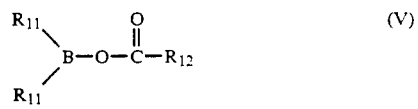

in which R$_{11}$ and R$_{12}$ represent a C$_1$-C$_6$ alkyl residue. This compound is obtained according to the procedure described by L. H. TOPORCER et al., J. Am. Chem. Soc. 87, 1236 (1965). Its isolation and purification are not necessary for carrying out the condensation of the aldehyde (III) with the cyclanone (IV).

The condensation reaction is performed at a temperature of approximately 150° C., without a solvent.

II. Second process

This process consists in condensing a Mannich base of formula (VI):

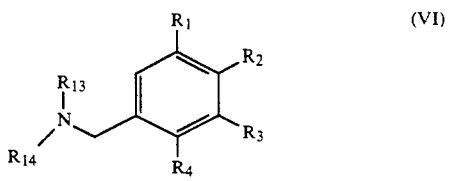

with a cyclanone of formula (IV) above. The Mannich bases of formula (VI) in which the substituents $R_1$ to $R_4$ have the meanings as stated above for the compounds of formula (I') and $R_{13}$ and $R_{14}$ represent a $C_1$-$C_4$ alkyl residue, or alternatively $R_{13}$ and $R_{14}$, with the nitrogen atom to which they are attached, form a heterocycle containing 5 or 6 atoms, are known compounds.

The condensation is performed in the presence of an alkali metal alcoholate such as sodium methylate or potassium tert-butylate, in a solvent such as ethylene glycol, 1,2-dimethoxyethane or 1,2-diethoxyethane, at a temperature between $-78°$ C. and the boiling point of the solvent.

The compounds of formula (I') may be isolated in the form of pure optical isomers or alternatively in the form of a racemic mixture.

The subject of the present invention is hence also the process for preparing the new compounds of formula (I').

Another subject of the invention is a cosmetic composition comprising, in a cosmetically acceptable vehicle, an effective amount of at least one benzylcyclanone derivative of formula (I) above.

The cosmetic composition of the invention may be used as a composition for protecting the human epidermis or the hair.

The subject of the present invention is also a process for protecting the skin and natural or sensitized hair, consisting in applying thereto an effective amount of at least one compound of formula (I) contained in a cosmetically acceptable vehicle.

"Sensitized hair" is understood to mean hair which has undergone a permanent-waving, dyeing or bleaching treatment.

The subject of the invention is also a coloured or uncoloured cosmetic composition, stabilized to oxidation, comprising an effective amount of at least one benzylcyclanone derivative of formula (I) above.

When used as a composition intended for protection of the human epidermis, the cosmetic composition according to the invention may be presented in the most diverse forms customarily used for this type of composition. It may, in particular, be presented in the form of lotions, of emulsions such as a cream or milk, of oleoalcoholic or aqueous-alcoholic gels, or of solid sticks, or be packaged as an aerosol to form a spray or a foam.

It can contain the cosmetic adjuvants customarily used in this type of composition, such as thickeners, emollients, humectants, surfactants, preservatives, antifoams, fragrances, oils, waxes, lanolin, propellants, colourings and/or pigments whose function is to colour the composition itself or the skin, or any other ingredient customarily used in cosmetics.

The compound of formula (I) is present in proportions of between 0.1 and 8% and preferably 0.1 and 5%, by weight relative to the total weight of the cosmetic composition for protecting the human epidermis.

An embodiment of the invention is an emulsion in the form of a protective cream or milk comprising, in addition to the compound of formula (I), fatty alcohols, fatty acid esters and, in particular, fatty acid triglycerides, fatty acids, lanolin, natural or synthetic oils or waxes and emulsifiers, in the presence of water.

The cosmetic composition of the invention can also be an aqueous-alcoholic or oleoalcoholic gel comprising one or more lower alcohols or polyols such as ethanol, propylene glycol or glycerol and a thickener. The oleoalcoholic gels contain, in addition, a natural or synthetic oil or wax.

The solid sticks consist of natural or synthetic waxes and oils, fatty alcohols, fatty acid esters, lanolin and other fats.

The present invention also relates to antisun cosmetic compositions containing at least one compound of formula (I) and UV-B and UV-A screening agents.

In this case, the quantity of compound of formula (I) is between 0.1 and 8% by weight, the total quantity of screening agents present in the antisun composition being between 0.5 and 15% by weight relative to the total weight of the antisun composition.

When the cosmetic composition according to the invention is intended for the protection of natural or sensitized hair, this composition may be presented in the form of a shampoo, lotion, gel or emulsion to be rinsed, to be applied before or after shampooing, before or after dyeing or bleaching and before or after permanent-waving, a styling or treatment lotion or gel, a blow-drying or setting lotion or gel, a hair lacquer or a permanent-waving, hair dyeing or bleaching composition.

It contains 0.25 to 8% by weight of compound of formula (I).

The present invention also relates to cosmetic compositions containing at least one compound of formula (I) by way of an antioxidant agent consisting of hair-care compositions such as hair lacquers, setting lotions, optionally with a treating or disentangling action, shampoos, colouring shampoos or hair dyeing compositions, or of makeup products such as nail varnishes, treatment creams and oils for the epidermis, foundations, lipsticks or skin-care compositions such as bath oils or creams, as well as any other cosmetic composition capable of suffering problems of stability to oxidation during storage as a result of its constituents.

Such compositions contain 0.1 to 8% by weight of compound of formula (I).

The invention also relates to a process for protecting cosmetic compositions against oxidation, consisting in incorporating an effective amount of at least one compound of formula (I) in these compositions.

Another subject of the invention is the use of the compounds of formula (I) as antioxidant agents.

The antioxidant effect of these compounds may be demonstrated by chemiluminescence of cell homogenates. This technique is based on the spontaneous emission of light which results from the radiative deactivation of the decomposition products of peroxidized lipids. The kinetic study is performed on ground preparations of rat . brain, diluted in a phosphate buffer, and is carried out in parallel with a control solution not containing antioxidant and solutions containing the antioxidant at different concentrations varying from $10^{-7}$ to $10^{-5}$ molar.

By reference to the control, it is possible to determine the antioxidant concentrations $C_x$ permitting an x% inhibition of peroxidation.

The subject of the invention is also the application of the compounds of formula (I) by way of cosmetic products.

As stated above, the Applicant also discovered in the course of his investigations that the compounds of formula (I) displayed advantageous pharmacological activity in the field of the treatment of skin allergies and inflammations.

The subject of the invention is hence the compound of formula (I) for its use as a medicinal product.

The subject of the invention is also a pharmaceutical composition containing an effective amount of at least one compound of formula (I) by way of an active ingredient, in a non-toxic vehicle or excipient.

The pharmaceutical composition according to the invention may be administered orally or topically.

For the oral route, the pharmaceutical composition may be presented in the form of tablets, hard gelatin capsules, dragées, syrups, suspensions, solutions, emulsions and the like. For topical application, the pharmaceutical composition according to the invention is presented in the form of an ointment, cream, pomade, solution, lotion, gel, spray, suspension, and the like.

This medicinal composition can contain inert or pharmacodynamically active additives, and in particular: moisturizing agents, antibiotics, steroidal or non-steroidal anti-inflammatory agents, carotenoids and antipsoriatic agents.

This composition can also contain flavour-improving agents, preservatives, stabilizers, moisture regulators, pH regulators, osmotic pressure-modifying agents, emulsifiers, local anaesthetics, buffers, and the like.

It can also be packaged in retard or sustained-release forms known per se.

The compound of formula (I) according to the invention is present in the pharmaceutical compositions in proportions of between 0.01 and 80% by weight relative to the total weight of the composition, and preferably between 0.1 and 20% by weight.

In the therapeutic application, the treatment is determined by the doctor and can vary according to the patient's age, weight and response as well as the severity of the symptoms.

When the compounds of formula (I) are administered orally, the dosage is generally between 0.1 and 50 mg/kg/day, and preferably between 0.2 and 20 mg/kg/day. The treatment period is variable according to the severity of the symptoms, and can range between 1 and 25 weeks, continuously or discontinuously.

The compositions for topical administration preferably contain from 0.25% to 8% by weight of compound of formula (I).

As a vehicle or excipient for the pharmaceutical composition of the invention, all non-toxic conventional vehicles or excipients may be used.

The examples which follow are intended as an illustration of the invention, no limitation of the latter being implied.

PREPARATION EXAMPLES

Example 1

Preparation of the compound of formula (I) in which $R_1=R_2=R_3=OH$, $R_4=H$, $R_5=R_6=R_7=R_8=CH_3$ and $X=O$

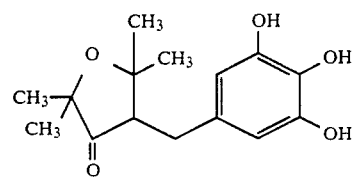

1) Preparation of 3',4',5'-tribenzyloxy-4-benzylidenetetrahydro-2,2,5,5-tetramethyl-3-furanone 5.4 g (0.1 mole) of sodium methylate and then 39.8 g (0.094 mole) of 3,4,5-tribenzyloxy-4-benzaldehyde in 100 cm³ of 1,2-dimethoxyethane are added at between 5° and 10° C. to a solution of 14.2 g (0.1 mole) of tetrahydro-2,2,5,5-tetramethyl-3-furanone in 20 cm³ of 1,2-dimethoxyethane. The reaction mixture is stirred for 30 minutes at a temperature in the region of 0° C., and the reaction mixture is then poured into dilute hydrochloric acid solution. The precipitate is filtered off, washed copiously with water and then with hot heptane and dried under reduced pressure. 35.8 g of expected product possessing the following properties are obtained:

Melting point: 73°–75° C.

| Elemental analysis: $C_{36}H_{36}O_5$ | | | |
|---|---|---|---|
| | C % | H % | O % |
| Calculated | 78.81 | 6.61 | 14.58 |
| Found | 78.78 | 6.61 | 14.64 |

UV spectrum ($CH_2Cl_2$)
$\lambda_{max}$: 340 nm.
$\epsilon_{max}$: 11400.

2) Preparation of 3',4',5'-trihydroxy-4-benzyltetrahydro-2,2,5,5-tetramethyl-3-furanone 5 g (0.009 mole) of 3',4',5'-tribenzyloxy-4-benzylidenetetrahydro-2,2,5,5-tetramethyl-3-furanone obtained above, in 50 cm³ of a 50:50 mixture of ethanol and tetrahydrofuran containing 5 g of ammonium formate and 0.5 g of palladium hydroxide, are heated to reflux for one hour. The reaction mixture is allowed to cool and then filtered on Celite. The Celite cake is washed with a 50:50 mixture of ethanol and tetrahydrofuran. The solvent is distilled off under reduced pressure and the residue is recrystallized in 50% ethanol.

The product obtained possesses the following properties:

Melting point: 186° C.

| Elemental analysis: $C_{15}H_{20}O_5$ | | | |
|---|---|---|---|
| | C % | H % | O % |
| Calculated | 64.27 | 7.19 | 28.54 |
| Found | 64.54 | 6.60 | 28.76 |

Example 2

Preparation of the compound of formula (I) in which $R_1=R_3=$tert-butyl, $R_2=$OH, $R_4=$H, $R_5=R_6=R_7=R_8=CH_3$ and $X=O$

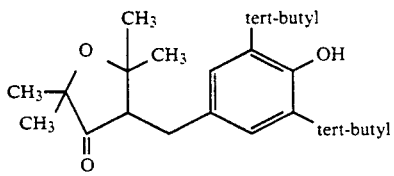

1) Preparation of 3'5'-di-tert-butyl-4'-hydroxy-4-benzylidenetetrahydro-2,2,5,5-tetramethyl-3-furanone 8.2 g (0.08 mole) of pivalic acid are added at 0° C. to 100 cm³ of a 1M solution of triethylborane in hexane. After 15 minutes' stirring, the mixture is allowed to return to room temperature and 5.4 g (0.038 mole) of tetrahydro-2,2,5,5-tetramethyl-3-furanone and 8.9 g (0.038 mole) of 3,5-di-tert-butyl-4-hydroxybenzaldehyde are then added. The hexane is distilled off and the mixture is heated to 150° C. for 3 hours. The volatile products are distilled off under reduced pressure 2 kPa and then 13 Pa). After recrystallization of the residue in an ethanol/water mixture, 5.5 g of expected product are obtained in the form of pale yellow crystals possessing the following properties:

Melting point: 146° C.

| Elemental analysis: $C_{23}H_{34}O_3$ | | | |
|---|---|---|---|
| | C % | H % | O % |
| Calculated | 77.05 | 9.56 | 13.39 |
| Found | 76.65 | 9.56 | 13.78 |

UV spectrum (CH₂Cl₂)
$\lambda_{max}$: 335 nm.
$\epsilon_{max}$: 18170.

Preparation of 3',5'-di-tert-butyl-4'-hydroxy-4-benzyltetrahydro-2,2,5,5-tetramethyl-3-furanone 3 g (0.0083 mole) of 3',5'-di-tert-butyl-4'-hydroxy-4-benzylidenetetrahydro-2,2,5,5-tetramethyl-3-furanone, obtained above, are suspended under argon in 50 cm³ of formic acid. 4 g of palladium on charcoal containing 50% of water (5% by weight of palladium relative to the charcoal) are added. The mixture is stirred for 1 hour at room temperature and then filtered on Celite after dilution with 50 cm³ of water. The Celite cake is washed several times with dichloromethane. The organic phase is separated after settling has taken place and then dried over sodium sulphate. The solvent is distilled off under reduced pressure. After recrystallization of the residue in diisopropyl ether, 0.8 g of expected product is obtained in the form of white crystals possessing the following properties:

Melting point: 104° C.

| Elemental analysis: $C_{23}H_{36}O_3$ | | | |
|---|---|---|---|
| | C % | H % | O % |
| Calculated | 76.62 | 10.06 | 13.31 |
| Found | 76.69 | 10.18 | 13.50 |

Example 3

Preparation of the compound of formula (I) in which $R_1=R_3=$tert-butyl, $R_2=$OH, $R_4=$H, $R_5=$H, $R_6-R_8=-CH_2-CH_2-$, $R_7=H_3$ and $X=-C(CH_3)_2-$

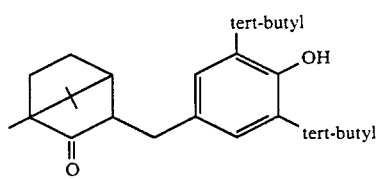

1) Preparation of 3',5'-di-tert-butyl-4'-hydroxy-3-benzylidenecamphor

This compound is prepared according to the procedure described in the first part of Example 2. Tetrahydro-2,2,5,5-tetramethyl-3-furanone is replaced by dl-camphor.

The expected product is obtained in the form of white crystals after recrystallization in diisopropyl ether. It possesses the following properties:

Melting point: 158° C.

| Elemental analysis: $C_{25}H_{36}O_2$ | | | |
|---|---|---|---|
| | C % | H % | O % |
| Calculated | 81.47 | 9.84 | 8.60 |
| Found | 81.37 | 9.84 | 8.78 |

UV spectrum (CHCl₃)
$\lambda_{max}$: 323 nm
$\epsilon_{max}$: 24200.

2) Preparation of 3',5'-di-tert-butyl-4'-hydroxy-3-benzylcamphor

2a) Preparation of a mixture of isomers, preponderantly exo 3 g (0.008 mole) of 3',5'-di-tert-butyl-4'-hydroxy-3-benzylidenecamphor, obtained above, are suspended under argon in 50 cm³ of formic acid. 4 g of palladium on charcoal containing 50% of water (5% by weight of palladium relative to the charcoal) are added. The mixture is stirred for 1 hour at room temperature and then filtered on Celite after dilution with 50 cm³ of water. The Celite cake is washed several times with dichloromethane. The organic phase is separated after settling has taken place and then dried over sodium sulphate. The solvent is distilled off under reduced pressure. After recrystallization of the residue in diisopropyl ether, 1.9 g of expected product are obtained in the form of white crystals, consisting of a mixture of isomers comprising a preponderance of the exo form, possessing the following properties:

Melting point: 166° C.

| Elemental analysis: $C_{25}H_{38}O_2$ | | | |
|---|---|---|---|
| | C % | H % | O % |
| Calculated | 81.03 | 10.34 | 8.64 |
| Found | 80.81 | 10.14 | 9.17 |

2b) Preparation of a mixture of isomers, preponderantly endo

The above mixture of isomers (1.9 g) is dissolved in 14 cm³ of ethanol in the presence of 0.5 g of sodium methylate. The mixture is heated to reflux for 2 hours under argon. Thereafter, the reaction mixture is acidified with 2N hydrochloric acid; the expected product precipitates; it is filtered off. After recrystallization of the precipitate in an ethanol/water medium (90:10), white crystals are obtained consisting of a mixture of isomers containing a preponderance of the endo form, possessing the following properties:

Melting point: 166° C.

| Elemental analysis: $C_{25}H_{38}O_2$ | | | |
|---|---|---|---|
| | C % | H % | O % |
| Calculated | 81.03 | 10.34 | 8.64 |
| Found | 81.13 | 10.38 | 8.68 |

The two forms, endo and exo, have the same physicochemical properties.

Example 4

Preparation of a compound of formula (I) in which $R_1=CH_3$, $R_2=OH$, $R_3=$tert-butyl, $R_4=R_5=H$, $R_6-R_8=-CH_2CH_2-$, $R_7=CH_3$ and $X=-C(CH_3)_2-$

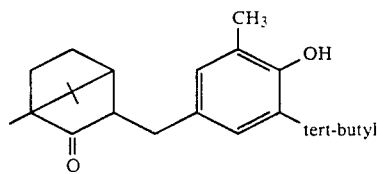

1) Preparation of 3'-tert-butyl-4'-hydroxy-5'-methyl-3-benzylidenecamphor 10.5 g (0.068 mole) of dl-camphor and 15.2 g (0.136 mole) of potassium tert-butylate in 100 ml of toluene are heated to reflux for 30 minutes. 13 g (0.068 mole) of 3-tert-butyl-4-hydroxy-5-methylbenzaldehyde are added at 80° C. and 80 cm³ of solvent are then distilled off. After 1 hour's heating, the reaction mixture is cooled to room temperature and then poured into aqueous hydrochloric acid solution. The product is extracted with dichloromethane. The organic phase is washed with water, dried over sodium sulphate and then evaporated to dryness.

The product is dispersed in heptane.

4.1 g of expected product are obtained in the form of very slightly beige crystals possessing the following properties:

Melting point: 152° C.

| Elemental analysis: $C_{22}H_{30}O_2$ | | |
|---|---|---|
| | C % | H % |
| Calculated | 80.94 | 9.26 |
| Found | 80.97 | 9.26 |

UV spectrum ($CH_2Cl_2$)
$\lambda_{max}$: 319 nm.
$\epsilon_{max}$: 23280.

2) Preparation of 3'-tert-butyl-4'-hydroxy-5'-methyl-3-benzylcamphor

This compound is prepared according to the procedure described in the second part of Example 3.

The expected product is obtained in the form of white crystals after recrystallization in heptane. It possesses the following properties:

Melting point: 147° C.

| Elemental analysis: $C_{25}H_{36}O_2$ | | | |
|---|---|---|---|
| | C % | H % | O % |
| Calculated | 80.44 | 9.82 | 9.74 |
| Found | 80.00 | 9.88 | 9.98 |

Example 5

Preparation of the compound of formula (I) in which $R_1=R_3=$tert-butyl, $R_2=OH$, $R_4=H$, $R_5=H$, $R_6-R_8=-CH_2-CH_2-$, $R_7=H$ and $X=-CH_2-$

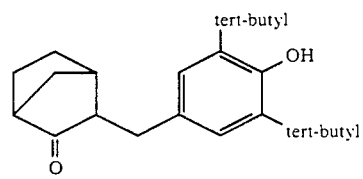

1) Preparation of 3',5'-di-tert-butyl-4'-hydroxy-3-benzylidenenorcamphor

This compound is prepared according to the procedure described in first part of Example 2. Tetrahydro-2,2,5,5-tetramethyl-3-furanone is replaced by norcamphor.

The expected product is obtained in the form of white crystals after recrystallization in heptane. It possesses the following properties:

Melting point: 134° C.

| Elemental analysis: $C_{25}H_{36}O_2$ | | | |
|---|---|---|---|
| | C % | H % | O % |
| Calculated | 80.94 | 9.26 | 9.80 |
| Found | 81.07 | 9.34 | 10.06 |

UV spectrum ($CH_2Cl_2$)
$\lambda_{max}$: 323 nm.
$\epsilon_{max}$: 24350.

2) Preparation of 3',5'-di-tert-butyl-4'-hydroxy-3-benzylnorcamphor

This compound is prepared according to the procedure described in the second part 2a) of Example 3.

The expected product is obtained in the form of white crystals after recrystallization in diisopropyl ether. It possesses the following properties:

Melting point: 112°–114° C.

| Elemental analysis: $C_{22}H_{32}O_2$ | | | |
|---|---|---|---|
| | C % | H % | O % |
| Calculated | 80.44 | 9.82 | 9.74 |
| Found | 79.86 | 9.86 | 10.22 |

Example 6

Preparation of a compound of formula (I) in which $R_1=R_3=OCH_3$, $R_2=OH$, $R_4=R_5=H$, $R_6-R_8=-CH_2-CH_2-$, $R_7=CH_3$ and $X=-C(CH_3)_2-$

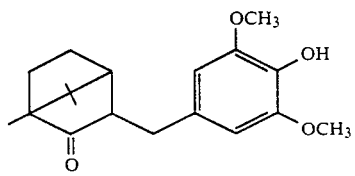

1) Preparation of 3',5'-dimethoxy-4'-hydroxy-3-benzylidenecamphor

This compound is obtained according to the procedure described in first part of Example 4 above, in which 3-tert-butyl-4-hydroxy-5-methylbenzaldehyde is replaced by 3,5-dimethoxy-4-hydroxybenzaldehyde.

The expected product is obtained in the form of white crystals after recrystallization in diisopropyl ether. It possesses the following properties:

Melting point: 158° C.

| Elemental analysis: $C_{19}H_{24}O_4$ | | | |
|---|---|---|---|
| | C % | H % | O % |
| Calculated | 72.13 | 7.65 | 20.23 |
| Found | 72.17 | 7.64 | 20.30 |

UV spectrum (dichloromethane)
$\lambda_{max}$: 327 nm.
$\epsilon_{max}$: 21300.

2) Preparation of 3',5'-dimethoxy-4'-hydroxy-3-benzylcamphor

This compound is prepared according to the procedure described in the second part 2a) of Example 3.

The expected product is obtained in the form of white crystals after recrystallization in diisopropyl ether. It possesses the following properties:

Melting point: 87° C.

| Elemental analysis: $C_{19}H_{26}O_4$ | | | |
|---|---|---|---|
| | C % | H % | O % |
| Calculated | 71.67 | 8.23 | 20.10 |
| Found | 71.57 | 8.23 | 20.18 |

Example 7

Preparation of a compound of formula (I) in which $R_1=R_3=$isopropyl, $R_2=OH$, $R_4=R_5=H$, $R_6-R_8=-CH_2-CH_2-$, $R_7=CH_3$ and $X=-C(CH_3)_2-$

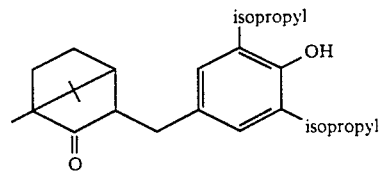

1) Preparation of 3',5'-diisopropyl-4'-hydroxy-3-benzylidenecamphor

This compound is obtained according to the procedure described in the first part of Example 4 above, in which 3-tert-butyl-4-hydroxy-5-methylbenzaldehyde is replaced by 3,5-diisopropyl-4-hydroxybenzaldehyde.

The expected product is obtained in the form of white crystals after recrystallization in diisopropyl ether. It possesses the following properties:

Melting point: 159°–160° C.

| Elemental analysis: $C_{23}H_{32}O_2$ | | | |
|---|---|---|---|
| | C % | H % | O % |
| Calculated | 81.13 | 9.47 | 9.40 |
| Found | 81.08 | 9.41 | 9.66 |

UV spectrum ($CH_2Cl_2$)
$\lambda_{max}$: 318 nm.
$\epsilon_{max}$: 25300.

2) Preparation of 3',5'-diisopropyl-4'-hydroxy-3-benzylcamphor

This compound is prepared according to the procedure described in the second part 2a) of Example 3.

The expected product is obtained in the form of white crystals after recrystallization in diisopropyl ether. It possesses the following properties:

Melting point: 122° C.

| Elemental analysis: $C_{23}H_{34}O_2$ | | | |
|---|---|---|---|
| | C % | H % | O % |
| Calculated | 80.65 | 10.01 | 9.34 |
| Found | 80.64 | 10.02 | 9.46 |

Example 8

Preparation of a compound of formula (I) in which $R_1=R_3=CH_3$, $R_2=OH$, $R_4=R_5=H$, $R_6-R_8=-CH_2CH_2-$, $R_7=CH_3$ and $X=-C(CH_3)_2-$

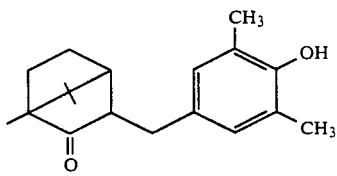

1) Preparation of 3',5'-dimethyl-4'-hydroxy-3-benzylidenecamphor

This compound is obtained according to the procedure described in the first part of Example 4 above, in which 3-tert-butyl-4-hydroxy-5-methylbenzaldehyde is replaced by 3,5-dimethyl-4-hydroxybenzaldehyde.

The expected product is obtained in the form of white crystals after recrystallization in diisopropyl ether. It possesses the following properties:

Melting point: 170° C.

| Elemental analysis: $C_{19}H_{24}O_2$ | | | |
|---|---|---|---|
| | C % | H % | O % |
| Calculated | 80.24 | 8.51 | 11.25 |
| Found | 80.21 | 8.50 | 11.28 |

UV spectrum ($CH_2Cl_2$)
$\lambda_{max}$: 318 nm.
$\epsilon_{max}$: 24100.

2) Preparation of 3',5'-dimethyl-4'-hydroxy-3-benzylcamphor

This compound is prepared according to the procedure described in the second part 2a) of Example 3.

The expected product is obtained in the form of white crystals after recrystallization in heptane. It possesses the following properties:

Melting point: 150° C.

| Elemental analysis: $C_{19}H_{26}O_2$ | | | |
|---|---|---|---|
| | C % | H % | O % |
| Calculated | 79.68 | 9.15 | 11.17 |
| Found | 79.61 | 9.09 | 11.34 |

Example 9

Preparation of a compound of formula (I) in which
$R_1=R_2=R_3=OH$, $R_4=R_5=H$,
$R_6-R_8=-CH_2-CH_2-$, $R_7=CH_3$ and
$X=-C(CH_3)_2-$

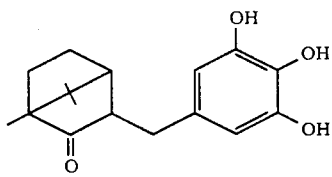

1) Preparation of 3',4',5'-tribenzyloxy-3-benzylidenecamphor

This compound is prepared according to the procedure described in the first part of Example 1. Tetrahydro-2,2,5,5-tetramethyl-3-furanone is replaced by dl-camphor.

The expected product is obtained in the form of white crystals after recrystallization in 95° strength ethanol. It possesses the following properties:

Melting point: 88° C.

| Elemental analysis: $C_{38}H_{38}O_4$ | | | |
|---|---|---|---|
| | C % | H % | O % |
| Calculated | 81.69 | 6.86 | 11.45 |
| Found | 81.60 | 6.87 | 11.51 |

2) Preparation of 3',4',5'-trihydroxy-3-benzylcamphor

This compound is prepared according to the procedure described in the second part 2a) of Example 3.

The expected product is obtained in the form of white crystals after recrystallization in diisopropyl ether. It possesses the following properties:

Melting point: 153° C.

| Elemental analysis: $C_{17}H_{22}O_4$ | | | |
|---|---|---|---|
| | C % | H % | O % |
| Calculated | 70.32 | 7.64 | 22.04 |
| Found | 70.26 | 7.66 | 22.09 |

Example 10

Preparation of the compound of formula (I) in which $R_1=OCH_3$, $R_2=H$, $R_3=$tert-butyl, $R_4=OH$, $R_4=OH$, $R_5=H$, $R_6-R_8=-CH_2-CH_2-$, $R_7=CH_2-SO_3H$ and $X=-C(CH_3)_2$

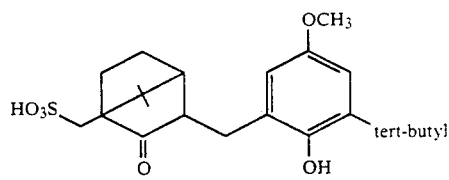

1) Preparation of 3'-tert-butyl-2'-hydroxy-5'-methoxy-3-benzylidene-10-camphorsulphonic acid 8.8 g (0.038 mole) of dl-10-camphorsulphonic acid, 6.1 g (0.114 mole) of sodium methylate and 7.9 g (0.038 mole) of 3-tert-butyl-2-hydroxy-5-methoxybenzaldehyde in 130 cm³ of 1,2-dimethoxyethane are heated to reflux for 1 hour. After cooling, 2 equivalents of 2N hydrochloric acid are added with stirring. The aqueous phase is saturated with sodium chloride. The product is extracted with dichloromethane and the solvent is then evaporated off. The yellow solid thereby obtained is dispersed while hot in diisopropyl ether. The product is filtered off and then dried under vacuum. The sodium salt thereby obtained is redissolved in water and the solution is filtered through a column of Dowex 50 ion exchange resin. After evaporation of the water under reduced pressure at room temperature, the expected compound is obtained in the form of an orange-coloured solid possessing the following properties:

| Elemental analysis: $C_{22}H_{30}O_6S$ | | | | |
|---|---|---|---|---|
| | C % | H % | O % | S % |
| Calculated | 62.54 | 7.16 | 22.72 | 7.59 |
| Found | 62.57 | 7.49 | 22.97 | 6.93 |

UV spectrum (in the form of the sodium salt, in water)
$\lambda_{max}1$: 295 nm.
$\epsilon_{max}1$: 11150.
$\lambda_{max}2$: 355 nm.
$\epsilon_{max}2$: 7500.

2) Preparation of
3'-tert-butyl-2'-hydroxy-5'-methoxy-3-benzyl-10-camphorsulphonic acid This compound is prepared according to the procedure described in the second part 2a) of Example 3.

The expected product is obtained in the form of white crystals after recrystallization in diisopropyl ether. It possesses the following properties:

Melting point: ≦250° C.

| Elemental analysis: $C_{22}H_{32}O_6S.\tfrac{1}{2}H_2O$ | | | | |
|---|---|---|---|---|
| | C % | H % | O % | S % |
| Calculated | 60.96 | 7.62 | 24.01 | 7.39 |
| Found | 61.23 | 7.97 | 24.18 | 6.60 |

Example 11

Preparation of the compound of formula (I) in which $R_1=R_3=$isopropyl, $R_2=$OH, $R_4=$H, $R_5=R_6=R_7=R_8=CH_3$ and $X=O$

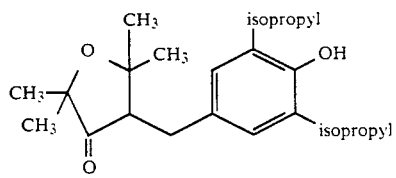

1) Preparation of
3',5'-diisopropyl-4'-hydroxy-4-benzylidenetetrahydro-2,2,5,5-tetramethyl-3-furanone:

This compound is obtained according to the procedure described in the first part of Example 1 above, in which 3,4,5-tribenzyloxy-4-benzaldehyde is replaced by 3,5-diisopropyl-4-hydroxybenzaldehyde.

The expected product is obtained in the form of a white solid. It possesses the following properties:

Melting point: 142° C.

| Elemental analysis: $C_{21}H_{30}O_3$ | | | |
|---|---|---|---|
| | C % | H % | O % |
| Calculated | 76.33 | 9.15 | 14.52 |
| Found | 76.57 | 9.23 | 14.68 |

UV spectrum (CH₂Cl₂)
$\lambda_{max}$: 335 nm.
$\epsilon_{max}$: 22400.

2) Preparation of
3',5'-diisopropyl-4'-hydroxy-4-benzyltetrahydro-2,2,5,5-tetramethyl-3-furanone This compound is prepared according to the procedure described in the second part of Example 3.

The expected product is obtained in the form of white crystals after recrystallization in heptane. It possesses the following properties:

Melting point: 90° C.

| Elemental analysis: $C_{21}H_{32}O_3$ | | | |
|---|---|---|---|
| | C % | H % | O % |
| Calculated | 75.86 | 9.70 | 14.44 |

-continued

| Elemental analysis: $C_{21}H_{32}O_3$ | | | |
|---|---|---|---|
| | C % | H % | O % |
| Found | 75.81 | 9.77 | 14.44 |

Example 12

Preparation of the compound of formula (I) in which $R_1=R_3=$tert-butyl, $R_2=$OH, $R_4=$H, $R_6-R_8=-CH_2-CH_2-$, $R_7=CH_3$ and $X=-C(CH_3)_2=$

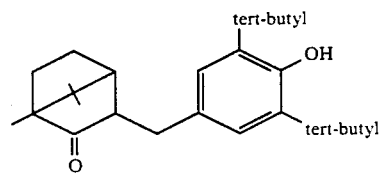

1) Preparation of 3',5'-di-tert-butyl-4'-hydroxy-3-benzylidenecamphor

This compound is prepared according to the procedure described in the first part of Example 2. Tetrahydro-2,2,5,5-tetramethyl-3-furanone is replaced by d-camphor.

The expected product is obtained in form of white crystals after recrystallization in diisopropyl ether. It possesses the following properties:

Melting point: 186° C.

| Elemental analysis: $C_{25}H_{36}O_2$ | | | |
|---|---|---|---|
| | C % | H % | O % |
| Calculated | 81.47 | 9.84 | 8.60 |
| Found | 81.40 | 9.87 | 8.79 |

UV spectrum (CHCl₃)
$\lambda_{max}$: 325 nm.
$\epsilon_{max}$: 23000.

2) Preparation of
3',5'-di-tert-butyl-4'-hydroxy-3-benzylcamphor (D)

This compound is prepared according to the procedure described in the second part of Example 3.

The expected product is obtained in the form of white crystals after recrystallization in a 95:5 ethanol/water mixture.

It possesses the following properties:
Melting point: 166° C.

| Elemental analysis: $C_{25}H_{38}O_2$ | | | |
|---|---|---|---|
| | C % | H % | O % |
| Calculated | 81.03 | 10.34 | 8.63 |
| Found | 81.22 | 10.29 | 8.79 |

Demonstration of the antioxidant properties of these compounds by chemiluminescence of cell homogenates The chemiluminescence test is conducted according to the publication by E. A. LISSI, T. CACERES and L. A. VIDELA "Visible Chemiluminescence from rat brain homogenates undergoing autoxidation. I. Effect of additives and products accumulation" in "Journal of Free Radicals in Biology and Medicine", Vol. 2, pp. 63–69 (1986). This test was simplified in the sense that only the chemiluminescence was measured, without measuring the accumulation of thiobarbituric acid after 1 hour's irradiation. However, according to the publication, there is good correlation between the chemiluminescence and the measurement of the accumulation of thiobarbituric acid.

Rat brains are removed immediately after cervical dislocation. They are washed with a buffer solution containing 140 mM NaCl and 40 mM potassium phosphate, relieved of the apparent vessels and the outer membrane and then ground with 4 times their volume of buffer solution. This ground preparation is diluted 3-fold with the buffer solution (total dilution 12-fold relative to the original organs).

10 ml of dilute homogenate are introduced into counting vials containing 200 µl of solution of the test antioxidant product, dissolved at different concentrations in methanol or dimethyl sulphoxide.

Immediately after shaking, the vials are introduced into a scintillation counter (BECKMAN) and counted periodically.

In parallel, a study is carried out on a control solution not containing antioxidant.

A curve for chemiluminescence intensity as a function of time is thereby established for each concentration.

By comparison of the slopes of the curves obtained with the solutions at different concentrations and the control solution, $C_{50}$, that is to say the antioxidant concentration permitting a 50% inhibition of peroxidation, is determined.

| | |
|---|---|
| Compound of Example 2: $C_{50} = 1.10 \times 10^{-6}$ M | |
| Compound of Example 3: $C_{50} = 2.00 \times 10^{-6}$ M | |
| Compound of Example 4: $C_{50} = 1.40 \times 10^{-6}$ M | |
| Compound of Example 5: $C_{50} = 1.50 \times 10^{-6}$ M | |
| Compound of Example 6: $C_{50} = 1.25 \times 10^{-6}$ M | |
| Compound of Example 7: $C_{50} = 0.80 \times 10^{-6}$ M | |
| Compound of Example 9: $C_{50} = 0.80 \times 10^{-6}$ M | |

By comparison, the $C_{50}$ of BHT (di-tert-butylhydroxytoluene), which is a traditional antioxidant, is $3.20 \times 10^{-6}$ M.

| Pharmaceutical compositions used topically | |
|---|---|
| Example A - Soothing ointment | |
| (To be applied on irritated skin in order to soothe) | |
| Compound of Example 3 | 2.0 g |
| Light liquid paraffin | 9.1 g |
| Silica sold by the company DEGUSSA under the name "AEROSIL 200" | 9.2 g |
| Isopropyl myristate | qs 100 g |
| Example B - Anti-inflammatory cream (oil-in-water) | |
| Compound of Example 6 | 2.5 g |
| Sodium dodecyl sulphate | 0.8 g |
| Glycerol | 2.0 g |
| Stearyl alcohol | 20.0 g |
| Triglycerides of capric/caprylic acid, sold by the company DYNAMIT NOBEL under the name "MIGLYOL 812" | 20.0 g |
| Preservative | qs |
| Demineralized water | qs 100 g |
| Example C - Soothing gel | |
| Compound of Example 7 | 1.5 g |
| Hydroxypropylcellulose sold by the company HERCULES under the name "KLUCEL HF" | 2.0 g |
| Ethanol | 70.0 g |
| Water | qs 100 g |
| Cosmetic composition | |
| Example D - Protective gel for the skin | |

| -continued | |
|---|---|
| Pharmaceutical compositions used topically | |
| Compound of Example 1 | 0.2 g |
| Glycerol | 12.0 g |
| Polyacrylic acid crosslinked with a polyfunctional agent, sold under the brandname "CARBOPOL 934" by the company GOODRICH | 0.8 g |
| Ethanol | 15.0 g |
| Preservative, fragrance | qs |
| Triethanolamine | qs pH 5.3 |
| Water, demineralized | qs 100 g |

We claim:

1. Benzylcyclanone derivative, of the formula:

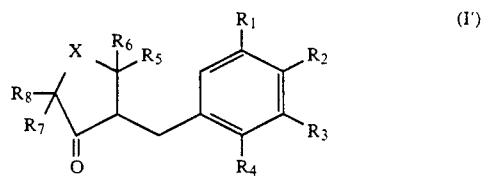

(I')

in which:

$R_1$ and $R_3$, which may be identical or different, represent a hydrogen atom, a hydroxyl radical, a linear or branched $C_1$-$C_8$ alkyl residue or a linear or branched $C_1$-$C_8$ alkoxy residue, $R_2$ and $R_4$, which may be identical or different, represent a hydrogen atom or a hydroxyl radical, on the understanding that at least one of the radicals $R_2$ and $R_4$ represents a hydroxyl radical, $R_5$, $R_6$, $R_7$ and $R_8$, which may be identical or different, represent a hydrogen atom, a linear or branched $C_1$-$C_{18}$ alkyl residue, an aralkyl residue, unsubstituted or substituted with a $C_1$-$C_4$ alkyl or $C_1$-$C_4$ alkoxy residue, or an aryl residue, unsubstituted or substituted with a $C_1$-$C_4$ alkyl residue; the substituents $R_5$ and $R_6$ and/or the substituents $R_7$ and $R_8$, with the carbon atom of the ring to which they are attached, can form a saturated ring containing from 5 to 12 carbon atoms, unsubstituted or substituted with one or more linear or branched $C_1$-$C_8$ alkyl residues, X represents an oxygen atom, $R_2$ a hydrogen atom and $R_4$ a hydroxyl radical, at least one of the radicals $R_1$ $R_3$ denotes a hydroxyl, alkyl or alkoxy radical.

2. Compound according to claim 1, selected from the group consisting of 3',4',5'-trihydroxy-4-benzyl-tetrahydro-2,2,5,5-tetramethyl-3-furanone, 3',5'-di-tert-butyl-4'-hydroxy-4-benzyltetrahydro-2,2,5,5-tetramethyl-3-furanone, and 3',5'-diisopropyl-4'-hydroxy-4-benzyltetra-hydro-2,2,5,5-tetramethyl-3-furanone.

3. Cosmetic or pharmaceutical composition, which comprises, in a cosmetically or pharmaceutically acceptable vehicle an effective amount of at least one compound of the formula:

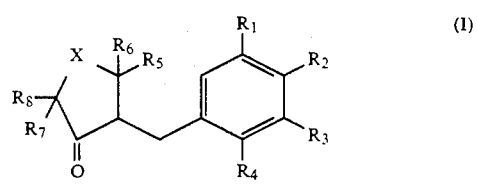

(I)

in which:

$R_1$ and $R_3$, which may be identical or different, represent a hydrogen atom, a hydroxyl radical, a linear or branched $C_1$–$C_8$ alkyl residue or a linear or branched $C_1$–$C_8$ alkoxy residue, $R_2$ and $R_4$, which may be identical of different, represent a hydrogen atom or a hydroxyl radical, on the understanding that at least one of the radicals $R_2$ and $R_4$ represents a hydroxyl radical, $R_5$, $R_6$, $R_7$ and $R_8$, which may be identical or different, represent a hydrogen atom, a linear or branched $C_1$–$C_{18}$ alkyl residue, an aralkyl residue, unsubstituted or substituted with a $C_1$–$C_4$ alkyl or $C_1$–$C_4$ alkoxy residue, or an aryl residue, unsubstituted or substituted with a $C_1$–$C_4$ alkyl residue; the substituents $R_5$ and $R_6$ and/or the substituents $R_7$ and $R_8$, with the carbon atom of the ring to which they are attached, can form a saturated ring containing from 5 to 12 carbon atoms, unsubstituted or substituted with one or more linear or branched $C_1$–$C_8$ alkyl residues, and X represents an oxygen atom.

4. Cosmetic or pharmaceutical composition according to claim 3, which comprises, by way of a compound (I) at least one compound selected from the group consisting of: 3',4',5'-trihydroxy-4-benzyltetrahydro-2,2,5,5-tetramethyl-3-furanone, 3',5'-di-tert-butyl-4'-hydroxy-4-benzyltetrahydro-2,2,5,5-tetramethyl-3-furanone, and 3',5'-diisopropyl-4'-hydroxy-4-benzyltetrahydro-2,2,5,5-tetramethyl-3-furanone.

5. Cosmetic composition according to claim 3, which is presented in the form of a lotion, emulsion, oleoalcoholic or aqueous-alcoholic gel, solid stick or aerosol.

6. Cosmetic composition according to claim 5, which contains, in addition, at least one cosmetic adjuvant selected from the group consisting of thickeners, emollients, humectants, surfactants, preservatives, antifoams, fragrances, oils, waxes, lanolin, lower monohydric alcohols and polyols, propellants, colourings and pigments.

7. Cosmetic composition according to claim 7 which constitutes a composition for protecting the human epidermis and contains 0.1 to 8% by weight of compound of formula (I).

8. Cosmetic composition according to claim 5, presented in the form of an antisun composition, which contains 0.1 to 8% by weight of compound of formula (I) and 0.5 to 15% by weight of UV-B and UV-A screening agents.

9. Cosmetic composition according to claim 3 or presented in the form of a coloured or uncoloured cosmetic composition, stabilized to oxidation, which consists of a hair-care composition, a makeup product or a skin-care or -treatment composition, comprising 0.1 to 8% by weight of compound of formula (I).

10. Cosmetic composition according to claim 3, intended for protection of the hair, which is presented in the form of a shampoo, a lotion, gel or emulsion to be rinsed, a styling or treatment lotion or gel, a blow-drying or setting lotion or gel, a hair lacquer or a permanent-waving, dyeing or bleaching composition, and which contains 0.25 to 8% by weight of compound of formula (I.

11. Process for protecting the skin, which consists of applying thereto an effective amount of a cosmetic composition containing at least one benzylcyclanone derivative of formula (I) according to claim 3.

12. Pharmaceutical composition according to claim 3, which comprises an effective amount of at least one compound of formula (I) in a nontoxic vehicle or excipient.

13. Pharmaceutical composition according to claim 3 intended for topical administration, presented in the form of a cream, ointment, pomade, solution, gel, lotion, spray or suspension, which contains an effective amount of at least one compound of formula (I).

14. Pharmaceutical composition according to claim 3 intended for oral administration in the form of tablets, hard gelatin capsules, dragées, syrups, suspensions, solutions or emulsions, which contains an effective amount of at least one compound of formula (I).

15. Pharmaceutical composition according to claim 13, which contains the compound of formula (I) in proportions of between 0.25 and 8% by weight relative to the total weight of the composition.

16. The compound according to claim 1 which is 3',5'-di-tert-butyl-4'-hydroxy-4-benzyltetrahydro-2,2,5,5-tetramethyl-3-furanone.

* * * * *